(12) United States Patent
Cosmescu

(10) Patent No.: US 12,285,204 B2
(45) Date of Patent: Apr. 29, 2025

(54) LAPAROSCOPIC ULTRAPOLAR ELECTROSURGERY DEVICE

(71) Applicant: I.C. Medical, Inc., Phoenix, AZ (US)

(72) Inventor: Ioan Cosmescu, Phoenix, AZ (US)

(73) Assignee: I.C. Medical, Inc., Phoenix, AZ (US)

( * ) Notice: Subject to any disclaimer, the term of this patent is extended or adjusted under 35 U.S.C. 154(b) by 42 days.

(21) Appl. No.: 18/323,740

(22) Filed: May 25, 2023

(65) Prior Publication Data

US 2023/0293227 A1  Sep. 21, 2023

Related U.S. Application Data

(63) Continuation of application No. 16/532,679, filed on Aug. 6, 2019.

(60) Provisional application No. 62/716,206, filed on Aug. 8, 2018.

(51) Int. Cl.
*A61B 18/14* (2006.01)
*A61B 18/08* (2006.01)
*A61B 18/00* (2006.01)

(52) U.S. Cl.
CPC ........ *A61B 18/1482* (2013.01); *A61B 18/082* (2013.01); *A61B 2018/00607* (2013.01); *A61B 2018/00922* (2013.01)

(58) Field of Classification Search
CPC .............. A61B 2218/002; A61B 18/12; A61B 2018/126; A61B 2018/00577; A61B 2018/00589; A61B 2018/00595; A61B 2018/00601; A61B 2018/00607; A61B 2018/0063; A61B 2017/00398; A61B 18/1482; A61B 2018/1475; A61B 2018/1405; A61B 1/3132; A61B 10/04; A61B 2017/22079; A61B 2017/22038; A61B 18/082; A61B 2018/00922; A61B 2018/00196; A61B 2018/00958; A61B 2018/1407; A61B 2018/1412; A61B 2018/142; A61B 2218/008
See application file for complete search history.

(56) References Cited

U.S. PATENT DOCUMENTS

| | | |
|---|---|---|
| 5,197,964 A | 3/1993 | Parins |
| 5,366,476 A | 11/1994 | Noda |
| 5,460,629 A | 10/1995 | Shlain et al. |
| 6,004,319 A | 12/1999 | Goble et al. |
| 6,267,761 B1 | 7/2001 | Ryan |
| 2004/0049217 A1 | 3/2004 | Ross et al. |
| 2012/0220848 A1 | 8/2012 | Razavi et al. |
| 2013/0172870 A1* | 7/2013 | Germain ................ A61B 18/18 606/115 |

(Continued)

FOREIGN PATENT DOCUMENTS

| | | |
|---|---|---|
| CN | 1929794 A | 3/2007 |
| CN | 110301947 A | 10/2011 |

(Continued)

*Primary Examiner* — Sean W Collins
(74) *Attorney, Agent, or Firm* — Zeman-Mullen & Ford, LLP

(57) ABSTRACT

A laparoscopic ultrapolar electrosurgery device having both active and return electrodes that reduces potential injury to patients during laparoscopic surgery by eliminating capacitive coupling when employing an electrosurgical handpiece device for cutting and/or coagulating tissue.

14 Claims, 4 Drawing Sheets

(56) References Cited

U.S. PATENT DOCUMENTS

| | | | |
|---|---|---|---|
| 2014/0303611 A1* | 10/2014 | Shadduck | A61B 18/148 606/33 |
| 2016/0135835 A1* | 5/2016 | Onuma | A61B 17/17 606/169 |
| 2020/0015876 A1 | 1/2020 | Chou et al. | |

FOREIGN PATENT DOCUMENTS

| CN | 202015228 U | 10/2011 |
|---|---|---|
| CN | 102395324 A | 3/2012 |
| CN | 107708591 A | 2/2018 |
| CN | 109640854 A | 4/2019 |
| EP | 136855 A2 | 4/1985 |
| VN | 109464189 A | 3/2019 |
| WO | 9724074 A1 | 7/1997 |

* cited by examiner

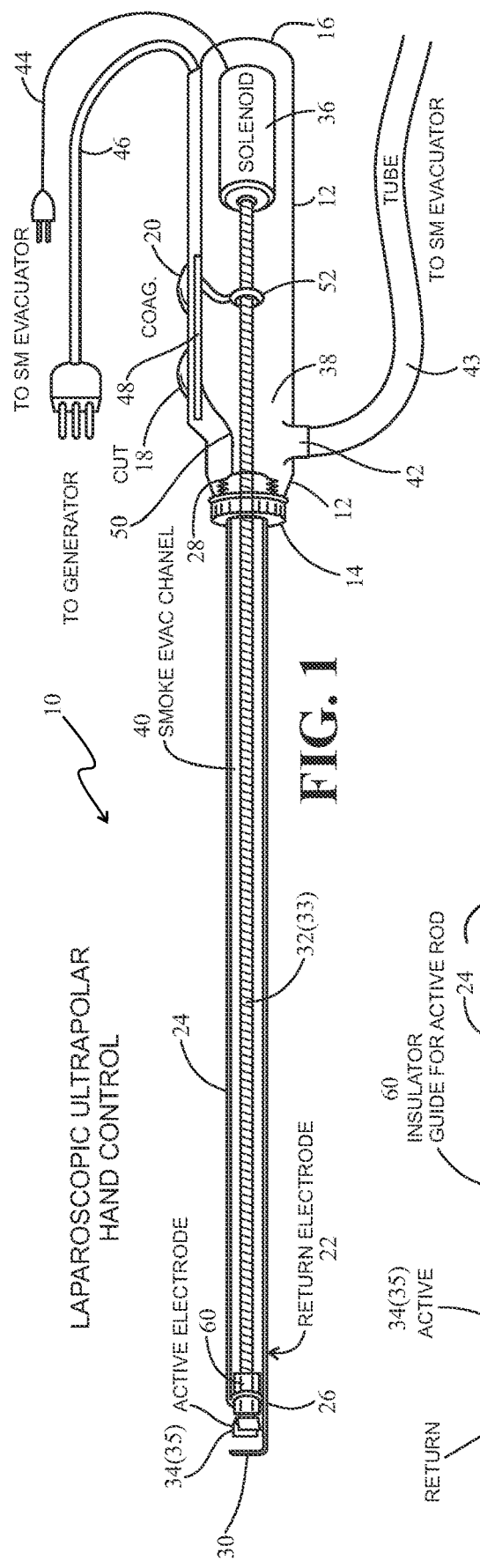
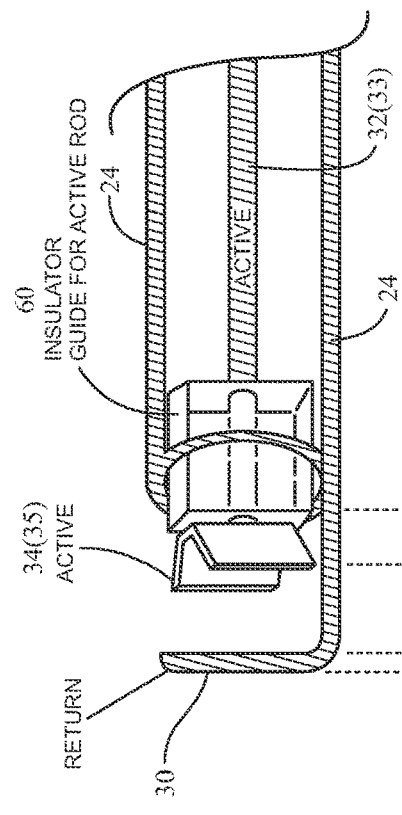
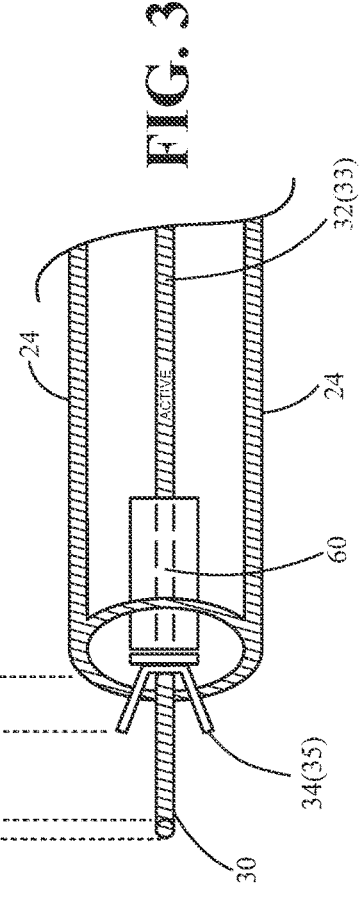
FIG. 1
FIG. 2
FIG. 3

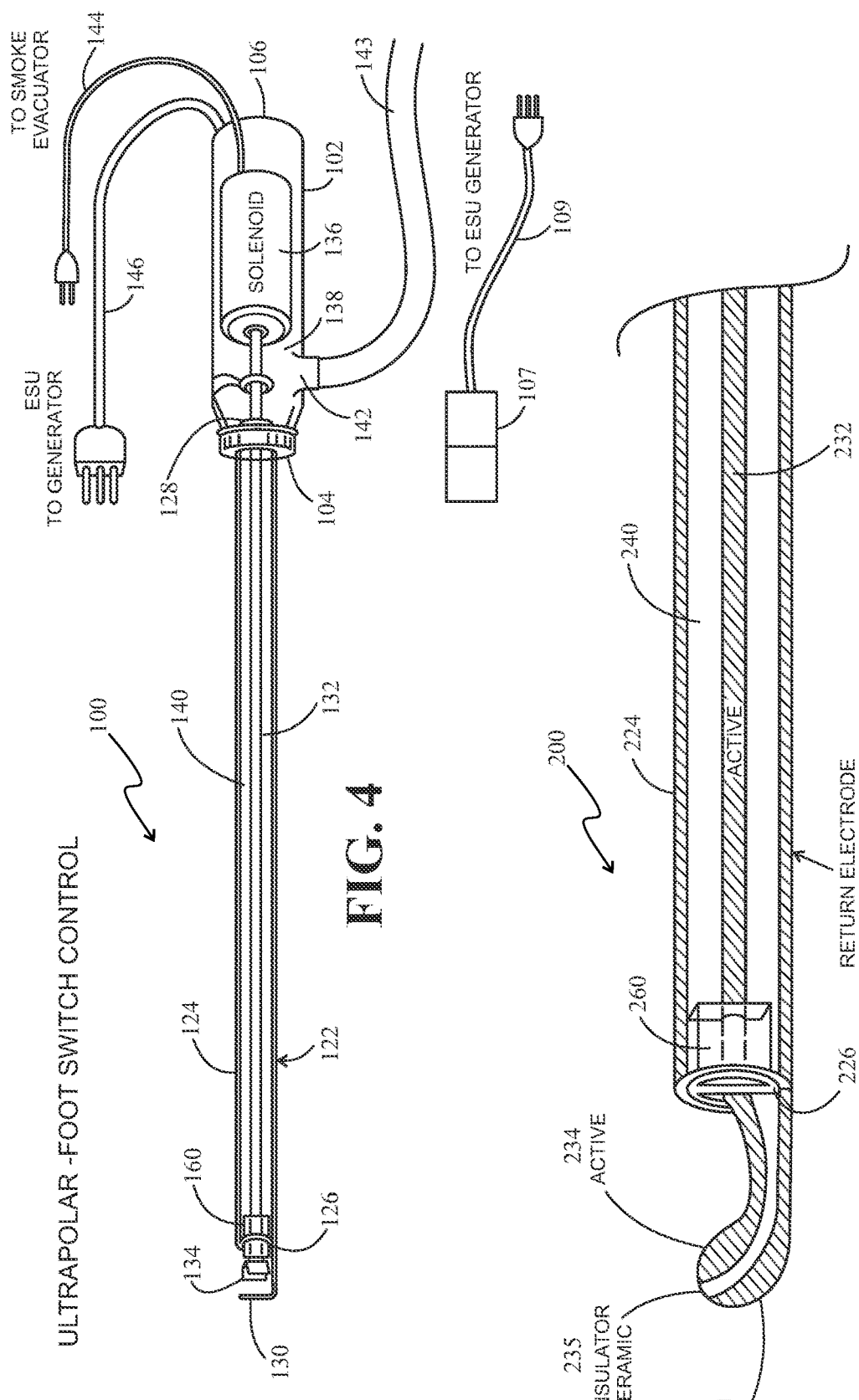

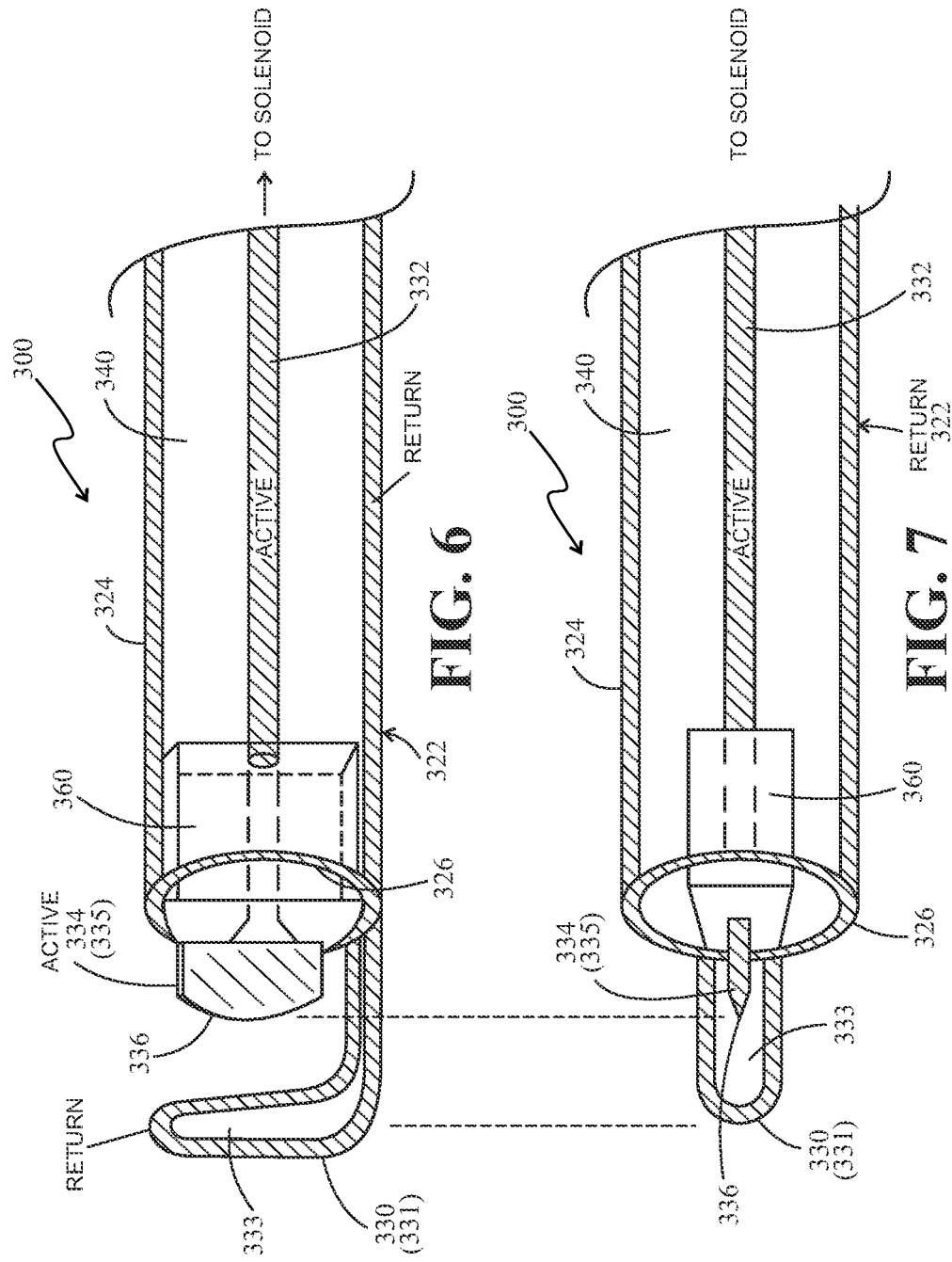

LAPAROSCOPIC ULTRAPOLAR ELECTROSURGERY DEVICE

CROSS-REFERENCE TO RELATED APPLICATIONS

This application claims priority to Non-provisional patent application having Ser. No. 16/532,679, filed Aug. 6, 2019, which claims priority to provisional patent application having Ser. No. 62/716,206, filed Aug. 8, 2018, which are herein incorporated by reference in their entireties.

FIELD OF INVENTION

The present invention is generally directed to a laparoscopic ultrapolar electrosurgery device for electrosurgical cutting and coagulation during laparoscopy. The laparoscopic ultrapolar electrosurgery device includes a handpiece member, a return electrode having a conductive hollow tubular member with first and second ends and a conductive appendage extending beyond the first conductive end, an active electrode contained within the handpiece member and suspended within the interior of the conductive hollow tubular member of the return electrode so that a portion of the active electrode extends beyond the first end of the conductive hollow tubular member of the return electrode to create an open space between the conductive appendage of the return electrode and the portion of the active electrode extending beyond the first end of the conductive hollow tubular member of the return electrode, and an actuator contained within the handpiece member in communication with the active electrode to move the active electrode toward the conductive appendage of the return electrode when the device is activated for cutting and/or coagulation.

BACKGROUND OF THE INVENTION

Laparoscopic surgery is a minimally invasive surgery in which surgical procedures are performed through small incisions with the assistance of a video camera. Trocars or cannulas are placed in the small incisions and the camera and other instruments are then introduced into the trocars or cannulas to access the inside of a patient. Many types of surgeries such as gastrointestinal surgery, gynecologic surgery and urology utilize laparoscopy. Laparoscopic surgeries minimize post-operative pain, speed up recovery times (and therefore shorten hospital stays), and result in less scarring.

Many laparoscopic procedures utilize electrosurgical techniques to dissect and coagulate tissue. Electrosurgery uses an RF electrosurgical generator (also known as an electrosurgical unit or ESU) and a handpiece with an electrode to provide high frequency, alternating radio frequency (RF) current input at various voltages to cut or coagulate biological tissue. The handpiece may be a monopolar instrument with one electrode or a bipolar instrument with two electrodes. When using a monopolar instrument, a return electrode pad is attached to the patient and the high frequency electrical current flows from the generator, to the monopolar instrument, through the patient to the patient return electrode pad, and back to the generator. Monopolar electrosurgery is commonly used due to its versatility and effectiveness. However, the excessive heat generated with monopolar electrosurgery can cause excessive tissue damage and necrosis of the tissue because the return electrode positioned on the back of the patient causes high voltage and high RF energy to pass through the patient.

Laparoscopic monopolar electrosurgery can cause indirect thermal injury when electrical current is conducted along unintended pathways and burns or vaporizes a non-targeted tissue. These indirect thermal injuries can occur as a result of direct coupling or capacitive coupling. Direct coupling can occur if the tip of the active electrode comes in direct contact with another metal instrument within the surgical field. For example, if the active electrode accidentally touches or arcs to the laparoscope, and the laparoscope has been placed in a nonconductive cannula, the entire laparoscope becomes electrified and the current on the laparoscope can be transferred to the patient's bowel or other internal tissue touching the laparoscope thereby resulting in thermal injury. Capacitive coupling occurs when energy is transferred through intact insulation to conductive materials. For example, current can leak through insulation surrounding an active electrode to another conductor such as a metal trocar which can result in a burn at an alternate site away from the surgical site. It is easy for even an experienced surgeon to miss a thermal injury resulting from capacitive coupling due to the limited view of the surgical field during laparoscopic procedures.

Accordingly, there is a need for a laparoscopic ultrapolar electrosurgery device that eliminates tissue damage and tissue necrosis by removing the need for a return electrode on the back of the patient so that no current passes through the patient's body during surgery. There is also a need for a laparoscopic ultrapolar electrosurgery device that reduces the chance for thermal injury to the patient by eliminating capacitive coupling and which requires less power to achieve cutting and coagulation than laparoscopic monopolar electrosurgery devices. The laparoscopic ultrapolar electrosurgery device of the present invention which includes both an active and return electrode within the same device meets these needs.

SUMMARY OF THE INVENTION

The present invention is directed to a laparoscopic ultrapolar electrosurgery device having both active and return electrodes which reduces potential injury to patients during laparoscopic surgery by eliminating capacitive coupling when employing an electrosurgical handpiece device for cutting and/or coagulating tissue.

In one exemplary embodiment, the laparoscopic ultrapolar electrosurgery device of the present invention includes a handpiece member having a first end, a second end, and at least one activation element for cutting and/or coagulation, a return electrode having a conductive hollow tubular member with a first end, a second end contained within the first end of the handpiece member, and a conductive appendage extending from the first end of the conductive hollow tubular member, an active electrode contained within the handpiece member and the conductive hollow tubular member with at least a portion of the active electrode extending beyond the first end of the conductive hollow tubular member, and an actuator contained within the handpiece member and in communication with the active electrode to move the active electrode toward the conductive appendage of the return electrode when activating cutting and/or coagulation. The handpiece member may further include a hollow area contained therein so that an interior of the conductive hollow tubular member and at least a portion of the hollow area contained in the handpiece together form a smoke evacuation channel.

The laparoscopic ultrapolar electrosurgery device of the present invention may further include a non-conductive guide member contained within at least a portion of the conductive hollow tubular member of the return electrode so that at least a portion of the active electrode is capable of moving or traversing through the non-conductive guide member. The non-conductive guide member may extend across an inner diameter of the conductive hollow tubular member near the first end of the conductive hollow tubular member to create two channels along opposing sides of the non-conductive guide member that are contiguous with an interior of the conductive hollow tubular member that surrounds the active electrode contained within the conductive hollow tubular member.

In one exemplary embodiment, the active electrode in the laparoscopic ultrapolar electrosurgery device of the present invention may comprise a curve shaped conductive member connected to a conductive rod member. The curve shaped conductive member may comprise a "U" or "V" shape and the curve shaped conductive member may be connected in perpendicular relationship to the conductive rod member with the interior of the "U" or "V" shape facing away from the conductive rod member. In another exemplary embodiment of the laparoscopic ultrapolar electrosurgery device of the present invention, an insulating material may be positioned between the conductive appendage of the return electrode and the portion of the active electrode that extends beyond the conductive hollow tubular member of the return electrode. In yet another exemplary embodiment of laparoscopic ultrapolar electrosurgery device of the present invention, the conductive appendage of the return electrode may comprise a conductive loop having an opening therethrough and the portion of the active electrode that extends beyond the conductive hollow tubular member of the return electrode may comprise a planar conductive member having a sharp edge.

The laparoscopic ultrapolar electrosurgery device of the present invention may further include an exhaust port connected to the conductive hollow tubular member of the return electrode so that the conductive hollow tubular member of the return electrode may also function as a smoke evacuation channel. The laparoscopic ultrapolar electrosurgery device may also include a connection member for connecting the actuator to a smoke evacuation device for simultaneously activating smoke evacuation when cutting and/or coagulation is activated.

In another exemplary embodiment of the laparoscopic ultrapolar electrosurgery device of the present invention, the device includes a handpiece member having a first end and a second end, a return electrode having a conductive hollow tubular member with a first end, a second end contained within the first end of the handpiece member, and a conductive appendage extending from the first end of the conductive hollow tubular member, an active electrode contained within the handpiece member and suspended within an interior of the conductive hollow tubular member so that at least a portion of the active electrode extends beyond the first end of conductive hollow tubular member to create an open space contained between the conductive appendage of the return electrode and the portion of the active electrode extending beyond the first end of the conductive hollow tubular member, and an actuator contained within the handpiece member and in communication with the active electrode to move the active electrode toward the conductive appendage of the return electrode when activating cutting and/or coagulation. The laparoscopic ultrapolar electrosurgery device may further include a floor switch in communication with the device to activate the device to perform cutting and/or coagulation.

The handpiece member of the laparoscopic ultrapolar electrosurgery device may also include a hollow area so that an interior of the conductive hollow tubular member and at least a portion of the hollow area contained within the handpiece together form a smoke evacuation channel. The laparoscopic ultrapolar electrosurgery device may further include a connection member for connecting the actuator to a smoke evacuation device for simultaneously activating smoke evacuation when cutting and/or coagulation is activated. In addition, the laparoscopic ultrapolar electrosurgery device may include a non-conductive guide member contained within at least a portion of the conductive hollow tubular member so that at least a portion of the active electrode is capable of moving through the non-conductive guide member.

BRIEF DESCRIPTION OF THE DRAWINGS

FIG. 1 is a side perspective view of an exemplary embodiment of the laparoscopic ultrapolar electrosurgery device of the present invention showing internal components of the device;

FIG. 2 is a partial magnified view of the cutting and coagulating end of the exemplary embodiment of the laparoscopic ultrapolar electrosurgery device shown in FIG. 1;

FIG. 3 is a top view of the partial magnified view of the cutting and coagulating end of the exemplary embodiment of the laparoscopic ultrapolar electrosurgery device shown in FIG. 2;

FIG. 4 is a side perspective view of another exemplary embodiment of the laparoscopic ultrapolar electrosurgery device of the present invention showing internal components of the device;

FIG. 5 is a partial side perspective view of the cutting and coagulating end of still another exemplary embodiment of the laparoscopic ultrapolar electrosurgery device of the present invention showing internal components of the device;

FIG. 6 is a partial side perspective view of the cutting and coagulating end of yet another exemplary embodiment of the laparoscopic ultrapolar electrosurgery device of the present invention showing internal components of the device;

FIG. 7 is a top view of the partial view of the cutting and coagulating end of the exemplary embodiment of the laparoscopic ultrapolar electrosurgery device shown in FIG. 6.

DETAILED DESCRIPTION OF EXEMPLARY EMBODIMENTS

Figure 8:
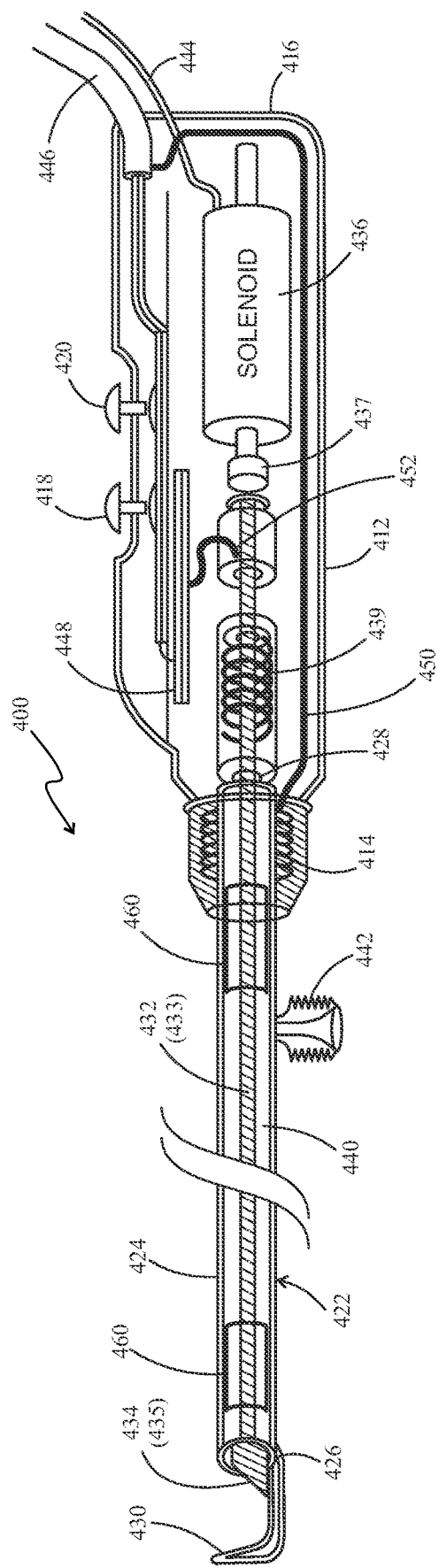
FIG. 8 is a side perspective view of still another exemplary embodiment of the laparoscopic ultrapolar electrosurgery device of the present invention showing internal components of the device.

The present invention is directed to a laparoscopic ultrapolar electrosurgery device which includes a handpiece member, a return electrode having a conductive hollow tubular member with one end connected to the handpiece member and the other end having a conductive appendage extending from it, and an active electrode contained within the handpiece member and suspended within an interior of the conductive hollow tubular member of the return electrode so that at least a portion of the active electrode extends beyond the end of the hollow tubular member of the return electrode having the conductive appendage. The laparoscopic ultrapolar electrosurgery device of the present invention is designed to eliminate the need for a return electrode to be placed on another part of the patient's body and further reduces the chance for thermal injury by eliminating capacitive coupling.

In one exemplary embodiment, as depicted in FIGS. 1-3, the laparoscopic ultrapolar electrosurgery device 10 of the present invention is a hand operated device having a handpiece member 12 with a first end 14, a second end 16, and at least one activation element 18,20 for cutting and/or coagulation, a return electrode 22 which includes a conductive hollow tubular member 24 having a first end 26, a second end 28 contained within or connected to the first end 14 of the handpiece member 12, and a conductive appendage 30 extending from the first end 26 of the conductive hollow tubular member 24, an active electrode 32 contained within the handpiece member 12 and the conductive hollow tubular member 24 of the return electrode 22 where at least a portion 34 of the active electrode 32 extends beyond the first end 26 of the conductive hollow tubular member 24 of the return electrode 22, and an actuator 36 contained within the handpiece member 12 and in communication with the active electrode 32 to move the active electrode 32 toward the conductive appendage 30 of the return electrode 22 when cutting and/or coagulation is activated. Active electrode 32 contained within the handpiece member 12 and the conductive hollow tubular member 24 of return electrode 22 may take the form of a solid conductive cylindrical member 33 while the portion 34 of the active electrode 32 that extends beyond the first end 26 of the conductive hollow tubular member 24 of return electrode 22 may take the form of a "U" or "V" shaped conductive element 35 that is connected to an end of the solid conductive cylindrical member 33 in a perpendicular relationship to the solid conductive cylindrical member 33.

The handpiece member 12 may further include a hollow area 38 contained therein such that the interior 40 of the conductive hollow tubular member 24 of the return electrode 22 together with at least a portion of the hollow area 38 within the handpiece member 12 form a smoke evacuation channel. The laparoscopic ultrapolar electrosurgery device 10 may further include a connection member 44 for connecting the actuator 36 to a smoke evacuation device (not shown) for simultaneously activating smoke evacuation when cutting and/or coagulation is activated. Handpiece member 12 may further include an exhaust outlet 42 in communication with the smoke evacuation channel within handpiece member 12. A vacuum tube 43 may then be connected to the exhaust outlet 42 while the other end of the vacuum tube 43 is connected to the smoke evacuation device (not shown). Both the connection member 44 (which is connected to actuator 36 within handpiece member 12) and vacuum tube 43 are connected to the same smoke evacuation device (not shown).

Laparoscopic ultrapolar electrosurgery device 10 further includes a circuit board 48, a first conductive communication means 50 (such as a wire or any other conductive connector) for connecting the return electrode 22 to the circuit board 48, a second conductive communication means 52 (such as a wire or any other conductive connector) for connecting the active electrode 32 to the circuit board 48, and a second connection member 46 (such as a cord containing one or more insulated wires) for connecting the laparoscopic ultrapolar electrosurgery device 10 to an electrosurgical generator to enable cutting and/or coagulation using the laparoscopic ultrapolar electrosurgery device 10. The activation elements for cutting and/or coagulation (such as buttons) 18,20 are positioned above circuit board 48 so that depressing the buttons engages the circuit board to provide for cutting and/or coagulation when utilizing the device 10.

The laparoscopic ultrapolar electrosurgery device 10 may further include a non-conductive guide member 60 contained within the conductive hollow tubular member 24 of return electrode 22 so that at least a portion of the active electrode 32 is capable of moving or traversing through the non-conductive guide member 60. The non-conductive guide member 60 may extend across the inner diameter of the conductive hollow tubular member 24 of return electrode 22 near the first end 26 of the conductive hollow tubular member 24 to create two channels along opposing sides of the non-conductive guide member 60 that are contiguous with an interior of the conductive hollow tubular member 24 that surrounds the active electrode 32 contained within the conductive hollow tubular member 24. As previously described above, the active electrode 32 may include a curve shaped conductive member 35 connected to a conductive rod member 33 and the curve shaped conductive member 35 may have a U or a V shape. Non-conductive guide member 60 ensures that portion 34 of active electrode 32 extending beyond the first end 26 of the conductive hollow tubular member 24 of return electrode 22 (such as curve shaped conductive member 35) can be steadily and securely moved toward conductive appendage 30 of return electrode 22 when the actuator 36 is activated and pushes conductive cylindrical rod member 33 of active electrode 32 toward the conductive appendage 30 of the return electrode 22.

When the device 10 is activated to perform cutting and/or coagulation, the actuator 36 (which may comprise a solenoid) is also activated. The actuator 36 functions to push the conductive cylindrical rod member 33 of the active electrode 32 forward which in turn moves the portion 34 of the active electrode 32 extending beyond the conductive hollow tubular member 24 of the return electrode 22 (e.g. the curve shaped conductive member 35) toward the conductive appendage 30 of the return electrode 22. A closed circuit is then created by the portion 34 of the active electrode 32 extending beyond the conductive hollow tubular member 24 of return electrode 22 (e.g. the curve shaped conductive member 35), the patient tissue needed to be cut, and the return electrode 22. The contact (and therefore the complete circuit) is made through the tissue. No current is traveling through the patient's body and much less power is needed to perform the cutting and/or coagulation using the device 10. In addition, since the active electrode 32 of the laparoscopic device 10 is contained within the return electrode 22 of the laparoscopic device 10, no capacitive coupling can take place between the patient and the laparoscopic device 10.

In another exemplary embodiment, as shown in FIG. 4, the laparoscopic ultrapolar electrosurgery device 100 of the present invention is a foot switch operated device having a handpiece member 102 with a first end 104 and a second end 106, a return electrode 122 which includes a conductive hollow tubular member 124 having a first end 126, a second end 128 contained within or connected to the first end 104 of the handpiece member 102, and a conductive appendage 130 extending from the first end 126 of the conductive hollow tubular member 124, an active electrode 132 contained within the handpiece member 102 and suspended within an interior 140 of the conductive hollow tubular member 124 so that at least a portion 134 of the active electrode 132 extends beyond the first end 126 of the conductive hollow tubular member 124 to create an open space contained between the conductive appendage 130 of the return electrode 122 and the portion 134 of the active electrode 132 extending beyond the first end 126 of the conductive hollow tubular member 124, and an actuator 136 contained within the handpiece member 102 and in communication with the active electrode 132 to move the active electrode 132 toward the conductive appendage 130 of the return electrode 122 when the device 100 is activated for cutting and/or coagulation. The device 100 may further include a floor switch 107 in communication with the device 100 to activate the device 100 to perform cutting and/or coagulation. Floor switch 107 may be connected to an electrosurgical generator unit (ESU) (not shown) by a connection member 109 to power device cutting/coagulation.

Like the embodiment shown in FIGS. 1-3, the handpiece member 102 may further include a hollow area 138 contained therein such that the interior of the hollow conductive tubular member together with at least a portion of the hollow area within the handpiece member form a smoke evacuation channel. The laparoscopic ultrapolar electrosurgery device 100 may further include a connection member 144 for connecting the actuator 136 to a smoke evacuation device (not shown) for simultaneously activating smoke evacuation when cutting and/or coagulation is activated. Handpiece member 102 may further include an exhaust outlet 142 in communication with the smoke evacuation channel within handpiece member 102. A vacuum tube 143 may then be connected to the exhaust outlet 142 while the other end of the vacuum tube 143 is connected to the smoke evacuation device (not shown). Both the connection member 144 (which is connected to actuator 136 within handpiece member 102) and vacuum tube 143 are connected to the same smoke evacuation device (not shown). The laparoscopic ultrapolar electrosurgery device 100 may also include a second connection member 146 (such as a cord containing one or more insulated wires) for connecting the laparoscopic ultrapolar electrosurgery device 100 to an electrosurgical generator (ESU) to enable cutting and/or coagulation using the laparoscopic ultrapolar electrosurgery device 100. Both the connection member 146 (which is connected to actuator 136 within handpiece member 102) and foot switch 107 are connected to the same electrosurgical unit (ESU) generator (not shown).

The laparoscopic ultrapolar electrosurgery device may further include a non-conductive guide member 160 contained within the conductive hollow tubular member 124 so that at least a portion of the active electrode 132 is capable of moving through/traversing through the non-conductive guide member 160. The non-conductive guide member 160 serves the same function as, and operates the same as, the non-conductive guide member 60 described above with reference to FIGS. 1-3.

FIG. 5 is a partial side perspective view of the cutting and coagulating end of still another exemplary embodiment of the laparoscopic ultrapolar electrosurgery device 200 of the present invention. As shown in FIG. 5, an insulating material 235, such as a ceramic, is contained between the conductive appendage 230 of the return electrode 222 and the portion 234 of the active electrode 232 extending beyond the first end 226 of the conductive hollow tubular member 224 of the return electrode 222. A non-conductive guide member 260 is contained within the conductive hollow tubular member 224 of the return electrode 222 to support the portion 234 of the active electrode 232 which extends beyond the first end 226 of the conductive hollow tubular member 224 of the return electrode 222. The portions of return electrode 230 and active electrode 234 that extend beyond the conductive hollow tubular member 224 of the return electrode 222, including the insulating material 235 contained between them, may be stationary and non-moveable. Alternatively, the portion 230 of return electrode 222 that extends beyond the conductive hollow tubular member 224 of the return electrode 222 may have a layer of the insulating material 235 contained thereon such that it is insulated from a moveable portion 235 of active electrode 232 that extends beyond the conductive hollow tubular member 224 of the return electrode 222.

FIGS. 6 and 7 show the cutting and coagulating end of yet another exemplary embodiment of the laparoscopic ultrapolar electrosurgery device 300 of the present invention. As shown in FIGS. 6 and 7, the conductive appendage 330 of the return electrode 322 is a conductive loop 331 having an opening 333 therethrough and the portion 334 of the active electrode 332 extending beyond the first end 326 of the conductive hollow tubular member 324 is a planar conductive member 335 having a sharp edge 336. The laparoscopic ultrapolar electrosurgery device 300 may further include a non-conductive guide member 360 contained within the conductive hollow tubular member 324 so that at least a portion of the active electrode 332 is capable of moving through/traversing through the non-conductive guide member 360. The non-conductive guide member 360 serves the same function as, and operates the same as, the non-conductive guide member 60 described above with reference to FIGS. 1-3.

In still another exemplary embodiment, as depicted in FIGS. 8, the laparoscopic ultrapolar electrosurgery device 400 of the present invention is a hand operated device having a handpiece member 412 with a first end 414, a second end 416, and at least one activation element 418,420 for cutting and/or coagulation, a return electrode 422 which includes a conductive hollow tubular member 424 having a first end 426, a second end 428 contained within or connected to the first end 414 of the handpiece member 412, and a conductive appendage 430 extending from the first end 426 of the conductive hollow tubular member 424, an active electrode 432 contained within the handpiece member 412 and the conductive hollow tubular member 424 where at least a portion 434 of the active electrode 432 extends beyond the first end 426 of the conductive hollow tubular member 424 of the return electrode 422, and an actuator 436 contained within the handpiece member 412 and in communication with the active electrode 432 to move the active electrode 432 toward the conductive appendage 430 of the return electrode 422 when cutting and/or coagulation is activated. The actuator 436 may have a push member 437 and a portion of the active electrode 432 located near the actuator 436 may be contained within a spring member 439 which assists in returning the active electrode 432 back to its pre-activated state after the push member 437 of the actuator 436 is retracted or disengaged from the end of the active electrode 432 contained within the handpiece member 412.

An exhaust outlet 442 may be connected to the conductive hollow tubular member 424 so that it is in communication with the interior 440 of the conductive hollow tubular member 424. The interior 440 of the conductive hollow tubular member 424 can then function as a smoke evacuation channel from which smoke and debris can be removed from the surgical site when a vacuum is attached to the exhaust outlet 442. The laparoscopic ultrapolar electrosurgery device 400 may further include a connection member 444 for connecting the actuator 436 to a smoke evacuation device (not shown) for simultaneously activating smoke evacuation when cutting and/or coagulation is activated.

The laparoscopic ultrapolar electrosurgery device 400 may further include one or more non-conductive guide members 460 contained within the conductive hollow tubular member 424 so that at least a portion of the active electrode 432 is capable of moving through the non-conductive guide member(s) 460. The non-conductive guide member(s) 460 may extend across the inner diameter of the conductive hollow tubular member 424 to create two channels along opposing sides of the non-conductive guide member(s) 460 that are contiguous with an interior 440 of the conductive hollow tubular member 424 that surrounds the active electrode 432 contained within the conductive hollow tubular member 424. The active electrode 432 includes a blade type member 435 connected to a conductive rod member 433.

When the device is activated to perform cutting and/or coagulation, the actuator 436 (which may comprise a solenoid) is also activated. The push member 437 of the actuator 436 functions to push the rod member 433 of the active electrode 432 forward which in turn moves the portion 434 of the active electrode 432 extending beyond the conductive hollow tubular member 424 of the return electrode 422 toward the conductive appendage 430 of the return electrode 422. A closed circuit is then created by the portion 434 of the active electrode 432 extending beyond the conductive hollow tubular member 424 of the return electrode 422, the patient tissue needed to be cut, and the return electrode 422. The contact (and therefore the complete circuit) is made through the tissue. No current is traveling through the patient's body and much less power is needed to perform the cutting and/or coagulation using the device 400. Also, since the active electrode 432 of the laparoscopic device 400 is contained within the return electrode 422 of the laparoscopic device 400, no capacitive coupling can take place between the patient and the laparoscopic device 400. The spring member 439 assists in returning the active electrode 432 back to its pre-activated state after the push member 437 of the actuator 436 is retracted or disengaged from the end of the active electrode 432 contained within the handpiece member 412.

The identity of the elements/features that relate to the numbers shown in the drawing figures are as follows:
- 10 laparoscopic ultrapolar electrosurgery device
- 12 handpiece member
- 14 first end (of handpiece member)
- 16 second end (of handpiece member)
- 18 activation element for cutting
- 20 activation element for coagulation
- 22 return electrode
- 24 conductive hollow tubular member
- 26 first end (of conductive hollow tubular member)
- 28 second end (of conductive hollow tubular member)
- 30 conductive appendage
- 32 active electrode
- 33 conductive cylindrical rod member
- 34 portion of active electrode (extending beyond first end of hollow conductive tubular member)
- 35 curve shaped conductive member
- 36 actuator (e.g. solenoid)
- 38 hollow area (within handpiece)
- 40 interior of conductive hollow tubular member
- 42 exhaust outlet (of handpiece)
- 43 vacuum tube
- 44 connection member (to/for smoke evacuator)
- 46 second connection member (to ESU generator for device cutting/coag)
- 48 circuit board
- 50 first conductive communication means (for connecting return electrode to circuit board)
- 52 second conductive communication means (for connecting active electrode to circuit board)
- 60 non-conductive guide member
- 100 laparoscopic ultrapolar electrosurgery device with foot switch control
- 102 handpiece member
- 104 first end (of handpiece member)
- 106 second end (of handpiece member)
- 107 foot switch
- 109 connection member (to ESU generator for device cutting/coag)
- 122 return electrode
- 124 conductive hollow tubular member
- 126 first end (of conductive hollow tubular member)
- 128 second end (of conductive hollow tubular member)
- 130 conductive appendage
- 132 active electrode
- 134 portion of active electrode (extending beyond first end of hollow conductive tubular member)
- 136 actuator (e.g. solenoid)
- 138 hollow area (within handpiece)
- 140 interior (of conductive hollow tubular member)
- 142 exhaust outlet (of handpiece)
- 143 vacuum tube
- 144 connection member (to/for smoke evacuator)
- 146 connection member (to ESU generator for device cutting/coag)
- 160 non-conductive guide member
- 200 laparoscopic ultrapolar electrosurgery device
- 222 return electrode
- 224 conductive hollow tubular member
- 226 first end (of conductive hollow tubular member)
- 230 conductive appendage
- 232 active electrode
- 234 portion of active electrode (extending beyond first end of hollow conductive tubular member)
- 235 insulating material (e.g. ceramic)
- 260 non-conductive guide member
- 300 laparoscopic ultrapolar electrosurgery device
- 322 return electrode
- 324 conductive hollow tubular member
- 326 first end (of conductive hollow tubular member)
- 330 conductive appendage
- 331 conductive loop
- 332 active electrode
- 333 opening
- 334 portion of active electrode (extending beyond first end of hollow conductive tubular member)
- 335 planar conductive member
- 336 sharp edge
- 360 non-conductive guide member
- 400 laparoscopic ultrapolar electrosurgery device
- 412 handpiece member
- 414 first end (of handpiece member)
- 416 second end (of handpiece member)
- 418 activation element for cutting
- 420 activation element for coagulation
- 422 return electrode
- 424 conductive hollow tubular member
- 426 first end (of conductive hollow tubular member)
- 428 second end (of conductive hollow tubular member)
- 430 conductive appendage
- 432 active electrode
- 433 conductive rod member
- 434 portion of active electrode (extending beyond first end of hollow conductive tubular member)
- 435 blade type member 436 actuator (e.g. solenoid)
437 push member (of actuator)
439 spring member
0 interior (of conductive hollow tubular member)
442 exhaust outlet (of conductive hollow tubular member for evacuating smoke and debris)
444 connection member (to/for smoke evacuator)
446 connection member (to ESU generator for device cutting/coag)
448 circuit board
450 conductive communication means (for connecting return electrode to connection member to ESU generator)
452 conductive communication means (for connecting active electrode to circuit board)
460 non-conductive guide member The above description of exemplary embodiments of the invention shows various exemplary embodiments of the invention. These exemplary embodiments and modes are described and shown in sufficient detail to enable those skilled in the art to practice the invention and are not intended to limit the scope, applicability, or configuration of the invention in any way. Rather, the disclosure is intended to teach both the implementation of the exemplary embodiments and modes and any equivalent modes or embodiments that are known or obvious to those reasonably skilled in the art. Additionally, all included examples are non-limiting illustrations of the exemplary embodiments and modes, which similarly avail themselves to any equivalent modes or embodiments that are known or obvious to those reasonably skilled in the art.

Other combinations and/or modifications of structures, arrangements, applications, proportions, elements, materials, or components used in the practice of the instant invention, in addition to those not specifically recited, can be varied or otherwise particularly adapted to specific environments, manufacturing specifications, design parameters, or other operating requirements without departing from the scope of the instant invention and are intended to be included in this disclosure.

Unless specifically noted, it is the Applicant's intent that the words and phrases in the specification and the claims be given the commonly accepted generic meaning or an ordinary and accustomed meaning used by those of ordinary skill in the applicable arts. In the instance where these meanings differ, the words and phrases in the specification and the claims should be given the broadest possible, generic meaning. If any other special meaning is intended for any word or phrase, the specification will clearly state and define the special meaning.

The invention claimed is:

1. A laparoscopic ultrapolar electrosurgery device comprising:
a handpiece member having a first end, a second end, and at least one of an activation element for cutting and an activation element for coagulation;
a return electrode comprising a conductive hollow tubular member having a first end, a second end contained within the first end of the handpiece member, and a conductive appendage extending from the first end of the conductive hollow tubular member wherein the conductive appendage comprises a conductive loop having an opening therethrough and a largest width of the conductive appendage is less than a diameter of the conductive hollow tubular member;
an active electrode contained within the handpiece member and the conductive hollow tubular member wherein at least a portion of the active electrode extends beyond the first end of the conductive hollow tubular member and comprises a planar conductive member having a sharp edge; and
an actuator contained within the handpiece member and in communication with the active electrode to move the active electrode toward the conductive appendage of the return electrode when at least one of cutting and coagulation is activated.

2. The laparoscopic ultrapolar electrosurgery device of claim 1 wherein the handpiece member further comprises a hollow area contained therein such that an interior of the conductive hollow tubular member and at least a portion of the hollow area contained within the handpiece together form a smoke evacuation channel.

3. The laparoscopic ultrapolar electrosurgery device of claim 2 further comprising a connection member for connecting the actuator to a smoke evacuation device for simultaneously activating smoke evacuation when at least one of cutting and coagulation is activated.

4. The laparoscopic ultrapolar electrosurgery device of claim 1 further comprising a non-conductive guide member contained within at least a portion of the conductive hollow tubular member such that at least a portion of the active electrode is capable of moving through the non-conductive guide member.

5. The laparoscopic ultrapolar electrosurgery device of claim 4 wherein the non-conductive guide member extends across an inner diameter of the conductive hollow tubular member close to or at the first end of the conductive hollow tubular member to create two channels along opposing sides of the non-conductive guide member that are contiguous with an interior of the conductive hollow tubular member that surrounds the active electrode contained within the conductive hollow tubular member.

6. The laparoscopic ultrapolar electrosurgery device of claim 1 wherein the active electrode comprises a curve shaped conductive member connected to a conductive rod member.

7. The laparoscopic ultrapolar electrosurgery device of claim 6 wherein the curve shaped conductive member comprises a U shaped conductive member or a V shaped conductive member.

8. The laparoscopic ultrapolar electrosurgery device of claim 6 further comprising a non-conductive guide member contained within at least a portion of the conductive hollow tubular member such that at least a portion of the conductive rod member is capable of moving through the non-conductive guide member.

9. The laparoscopic ultrapolar electrosurgery device of claim 1 further comprising an insulating material contained between the conductive appendage of the return electrode and the portion of the active electrode extending beyond the first end of the conductive hollow tubular member.

10. The laparoscopic ultrapolar electrosurgery device of claim 1 wherein the actuator comprises a solenoid.

11. The laparoscopic ultrapolar electrosurgery device of claim 1 further comprising an exhaust port connected to the conductive hollow tubular member so that the conductive hollow tubular member may also function as a smoke evacuation channel.

12. A laparoscopic ultrapolar electrosurgery device comprising:
a handpiece member having a first end, a second end, and at least one of an activation element for cutting and an activation element for coagulation;

a return electrode comprising a conductive hollow tubular member having a first end, a second end contained within the first end of the handpiece member, and a conductive appendage extending from the first end of the conductive hollow tubular member wherein the conductive appendage comprises a solid cylindrical member;

an active electrode contained within the handpiece member and the conductive hollow tubular member wherein at least a portion of the active electrode extends beyond the first end of the conductive hollow tubular member; and an actuator contained within the handpiece member and in communication with the active electrode to move the active electrode toward the conductive appendage of the return electrode when at least one of cutting and coagulation is activated.

13. The laparoscopic ultrapolar electrosurgery device of claim 12 further comprising a non-conductive guide member having a non-cylindrical shape contained within at least a portion of the conductive hollow tubular member of the return electrode such that is extends across an inner diameter of the conductive hollow tubular member.

14. The laparoscopic ultrapolar electrosurgery device of claim 13 wherein the non-conductive guide member extends across the inner diameter of the conductive hollow tubular member close to or at the first end of the conductive hollow tubular member to create two channels along opposing sides of the non-conductive guide member that are contiguous with an interior of the conductive hollow tubular member that surrounds the active electrode contained within the conductive hollow tubular member.

\* \* \* \* \*